United States Patent [19]

Halluin

[11] Patent Number: 5,023,078

[45] Date of Patent: Jun. 11, 1991

[54] PLASMINOGEN ACTIVATOR-HEPARIN CONJUGATES

[75] Inventor: Albert P. Halluin, 31 Willowview Ct., Danville, Calif. 94526

[73] Assignee: Albert P. Halluin, Danville, Calif.

[21] Appl. No.: 363,908

[22] PCT Filed: Aug. 10, 1988

[86] PCT No.: PCT/US88/02771

§ 371 Date: May 24, 1989

§ 102(e) Date: May 24, 1989

[87] PCT Pub. No.: WO90/01332

PCT Pub. Date: Feb. 22, 1990

[51] Int. Cl.$^5$ ............... A61K 37/547; A61K 31/725; C12N 9/50

[52] U.S. Cl. ................... 424/94.64; 435/219; 514/56; 514/822

[58] Field of Search ............ 424/94.63, 94.64; 435/219, 226, 215; 514/56, 822

[56] References Cited

U.S. PATENT DOCUMENTS

| | | | |
|---|---|---|---|
| 4,029,767 | 6/1977 | Vairel | 424/94.63 |
| 4,381,346 | 4/1983 | Huasin | 435/212 |
| 4,496,550 | 1/1985 | Lindahl | 536/21 |
| 4,500,519 | 2/1985 | Lormeau et al. | 514/822 |
| 4,692,435 | 9/1987 | Lormeau | 536/21 |
| 4,745,180 | 5/1988 | Moreland | 435/811 |
| 4,752,581 | 6/1988 | Robinson | 424/94.64 |
| 4,777,161 | 10/1988 | Lormeau | 536/21 |

FOREIGN PATENT DOCUMENTS 3361778 2/1978 Australia .
2119804 11/1983 United Kingdom .

OTHER PUBLICATIONS

Stassen, Thrombosis and Haemostasis (1987), 58(3), pp. 947–950.
Wang, Chem. Abstracts, vol. 101 (1984):188723u.
Andrade-Gordon, Biochemistry (1986), 25, 4033–4040.
Maksimenko, Thromb. Res. 38 (1985) pp. 277–288.
Matsuo (1982) Throm. Hemostasis 48:242.
Stump et al., (1987) J. Pharmacol. Exper. Therap. 242(1): 245–250.
Lau et al., (1987) Biotechnology 5:953–958.
Klausner (1986) Biotechnology 4(8):706–711.
Abstract of South American Application No. 551,782, filed Dec. 27, 1985.
Paques et al., (1986) Thromb. Res. 42:797–807.
Hoffman (1983) Carbohydrate Res. 117:328–331.
Bjork et al., (1982) FEBS Letters 143(1):96–100.

Primary Examiner—Jacqueline Stone
Attorney, Agent, or Firm—Lisabeth F. Murphy; Albert P. Halluin

[57] ABSTRACT

A pharmaceutical composition is prepared wherein a biologically active conjugated plasminogen activator is selectively conjugated to at least one heparin fragment having a terminal 2,5-anhydro-D-mannose residue which has an aldehyde not involved in intramolecular hemiacetal formation. The resulting conjugate has a prolonged half-life as compared to native tissue plasminogen activator and is able to deliver heparin to the site of clot dissolution to prevent reocclusion.

9 Claims, 4 Drawing Sheets

FIG. 1

Secretory Leader ⟶
M  A  L  A  I  T  L  A  L  L  L  L  L  L  L  L  P  G  C  W
ATGGCGTTAGCTATTACTCTTGCATTATTGCTTCTCCTACTGTTATTGCCTGGGTGTTGG
TACCGCAATCGATAATGAGAACGTAATAACGAAGAGGATGACAATAACGGACCCACAACC
1                                                          60

Plasminogen Kringle 1
      1
A  S  E | C  K  T  G  D  G  K  N  Y  R  G  T  M  S  K  T  K
GCTAGCGAATGCAAAACCGGTGACGGTAAAAACTACCGTGGTACCATGTCCAAAACCAAA
CGATCGCTTACGTTTTGGCCACTGCCATTTTTGATGGCACCATGGTACAGGTTTTGGTTT
                                                           120

20
N  G  I  T  C  Q  K  W  S  S  T  S  P  H  R  P  R  F  S  P
AACGGTATCACCTGCCAGAAATGGTCCTCCACCTCCCCGCACCGTCCGCGTTTCTCCCCG
TTGCCATAGTGGACGGTCTTTACCAGGAGGTGGAGGGGCGTGGCAGGCGCAAAGAGGGGC
                                                           180

40
A  T  H  P  S  E  G  L  E  E  N  Y  C  R  N  P  D  N  D  P
GCTACCCACCCGTCCGAAGGTCTGGAAGAAAACTACTGCCGTAACCCGGACAACGACCCG
CGATGGGTGGGCAGGCTTCCAGACCTTCTTTTGATGACGGCATTGGGCCTGTTGCTGGGC
                                                           240

60
Q  G  P  W  C  Y  T  T  D  P  E  K  R  Y  D  Y  C  D  I  L
CAGGGTCCGTGGTGCTACACCACCGACCCGGAAAAACGTTACGACTACTGCGACATCCTC
GTCCCAGGCACCACGATGTGGTGGCTGGGCCTTTTTGCAATGCTGATGACGCTGTAGGAG
                                                           300

FIG. 1 (cont.)

```
                    Linker                       scuPA
 80       |→                         |→
  E  C    E  E  E  P  S  S  P  P  E  E  L  K  F  Q   C  G  Q  K
  GAGTGCGAAGAAGAACCGTCCTCCCCGCCGGAAGAACTGAAATTCCAGTGCGGTCAGAAA
  CTCACGCTTCTTCTTGGCAGGAGGGGCGGCCTTCTTGACTTTAAGGTCACGCCAGTCTTT
                                                              360
```

Protease Domain
```
100
  T  L  R  P  R  F  K  I  I  G  G  E  F  T  T  I  E  N  Q  P
  ACCCTGCGGCCGCGCTTTAAGATTATTGGGGGAGAATTCACCACCATCGAGAACCAGCCC
  TGGGACGCCGGCGCGAAATTCTAATAACCCCCTCTTAAGTGGTGGTAGCTCTTGGTCGGG
                                                              420

120
  W  F  A  A  I  Y  R  R  H  R  G  G  S  V  T  Y  V  C  G  G
  TGGTTTGCGGCCATCTACAGGAGGCACCGGGGGGGCTCTGTCACCTACGTGTGTGGAGGC
  ACCAAACGCCGGTAGATGTCCTCCGTGGCCCCCCCGAGACAGTGGATGCACACACCTCCG
                                                              480

140
  S  L  I  S  P  C  W  V  I  S  A  T  H  C  F  I  D  Y  P  K
  AGCCTCATCAGCCCTTGCTGGGTGATCAGCGCCACACACTGCTTCATTGATTACCCAAAG
  TCGGAGTAGTCGGGAACGACCCACTAGTCGCGGTGTGTGACGAAGTAACTAATGGGTTTC
                                                              540

160
  K  E  D  Y  I  V  Y  L  G  R  S  R  L  N  S  N  T  Q  G  E
  AAGGAGGACTACATCGTCTACCTGGGTCGCTCAAGGCTTAACTCCAACACGCAAGGGGAG
  TTCCTCCTGATGTAGCAGATGGACCCAGCGAGTTCCGAATTGAGGTTGTGCGTTCCCCTC
                                                              600
```

FIG. 1 (cont.)

```
180
M  K  F  E  V  E  N  L  I  L  H  K  D  Y  S  A  D  T  L  A
ATGAAGTTTGAGGTGGAAAACCTCATCCTACACAAGGACTACAGCGCTGACACGCTTGCT
TACTTCAAACTCCACCTTTTGGAGTAGGATGTGTTCCTGATGTCGCGACTGTGCGAACGA
                                                         660

200
H  H  N  D  I  A  L  L  K  I  R  S  K  E  G  R  C  A  Q  P
CACCACAACGACATTGCCTTGCTGAAGATCCGTTCCAAGGAGGGCAGGTGTGCGCAGCCA
GTGGTGTTGCTGTAACGGAACGACTTCTAGGCAAGGTTCCTCCCGTCCACACGCGTCGGT
                                                         720

220
S  R  T  I  Q  T  I  C  L  P  S  M  Y  N  D  P  Q  F  G  T
TCCCGGACTATACAGACCATCTGCCTGCCCTCGATGTATAACGATCCCCAGTTTGGCACA
AGGGCCTGATATGTCTGGTAGACGGACGGGAGCTACATATTGCTAGGGGTCAAACCGTGT
                                                         780

240
S  C  E  I  T  G  F  G  K  E  N  S  T  D  Y  L  Y  P  E  Q
AGCTGTGAGATCACTGGCTTTGGAAAAGAGAATTCTACCGACTATCTCTATCCGGAGCAG
TCGACACTCTAGTGACCGAAACCTTTTCTCTTAAGATGGCTGATAGAGATAGGCCTCGTC
                                                         840

260
L  K  M  T  V  V  K  L  I  S  H  R  E  C  Q  Q  P  H  Y  Y
CTGAAAATGACTGTTGTGAAGCTGATTTCCCACCGGGAGTGTCAGCAGCCCCACTACTAC
CTGAAAATGAGACAACACTTCGACTAAAGGGTGGCCCTCACAGTCGTCGGGGTGATGATG
                                                         900
```

FIG. 1 (cont.)

```
280
G   S   E   V   T   T   K   M   L   C   A   A   D   P   Q   W   K   T   D   S
GGCTCTGAAGTCACCACCAAAATGCTGTGTGCTGCTGACCCACAGTGGAAAACAGATTCC
CCGAGACTTCAGTGGTGGTTTTACGACACACGACGACTGGGTGTCACCTTTTGTCTAAGG
                                                                    960

300
C   Q   G   D   S   G   G   P   L   V   C   S   L   Q   G   R   M   T   L   T
TGCCAGGGAGACTCAGGGGGACCCCTCGTCTGTTCCCTCCAAGGCCGCATGACTTTGACT
ACGGTCCCTCTGAGTCCCCCTGGGGAGCAGACAAGGGAGGTTCCGGCGTACTGAAACTGA
                                                                    1020

320
G   I   V   S   W   G   R   G   C   A   L   K   D   K   P   G   V   Y   T   R
GGAATTGTGAGCTGGGGCCGTGGATGTGCCCTGAAGGACAAGCCAGGCGTCTACACGAGA
CCTTAACACTCGACCCCGGCACCTACACGGGACTTCCTGTTCGGTCCGCAGATGTGCTCT
                                                                    1080

340
V   S   H   F   L   P   W   I   R   S   H   T   K   E   E   N   G   L   A   L
GTCTCACACTTCTTACCCTGGATCAGAAGTCACACCAAGGAAGAGAATGGCCTGGCCCTC
CAGAGTGTGAAGAATGGGACCTAGTCTTCAGTGTGGTTCCTTCTCTTACCGGACCGGGAG
                                                                    1140

TGA
ACT
```

PLASMINOGEN ACTIVATOR-HEPARIN CONJUGATES

FIELD OF THE INVENTION

The invention relates to a chemical modification of biologically active thrombolytic agents. More specifically, the invention relates to selective conjugation of plasminogen activators to heparin fragments to increase the half-life of the resulting conjugate.

BACKGROUND OF THE INVENTION

The formation of blood clots in blood vessels of major organs in the body is one of the leading causes of human mortality in Western industrialized society. Myocardial infarction—heart attack—primarily caused by blood clot formation or thrombosis in the coronary artery, is the leading cause of death in the United States among adult males. Emboli, blood clots traveling in the circulatory system, which lodge in the blood vessels of the lung, brain, or heart are also significant causes of death in patients following surgery, dialysis and traumatic injury. Phlebitis, a condition in which thrombi, stationary blood clots, block circulation through the large blood vessels, particularly of the lower extremities, is also a serious threatening disease.

The mechanism of blood clot dissolution or fibrinolysis is complex. At least three components are involved; plasminogen, plasminogen activators and plasmin inhibitors. Plasminogen is one of the circulating plasma proteins incorporated into a blood clot as it forms. Plasminogen is an inactive precursor or proenzyme form of the protein plasmin, a proteolytic enzyme that digests fibrin threads, as well as other substances involved in the activation of blood clot formation such as fibrinogen, factor V, factor VIII, prothrombin, and factor XII. Limited proteolysis of plasminogen yields plasmin. Plasminogen can be proteolytically activated to form plasmin by a number of enzymatically active proteins known as plasminogen activators. Plasminogen has a specific binding affinity for fibrin and thus a portion of the circulating plasminogen accumulates in the blood clot in association with the fibrin reticulum of the clot.

There are a number of commercially known plasminogen activators presently available for use in thrombolytic therapy including streptokinase, urokinase, recombinant tissue type plasminogen activator and acylated streptokinase-plasminogen. Streptokinase does not specifically bind to fibrin and as a result, it activates both circulating plasminogen and plasminogen in the blood clot. Two-chain urokinase is similar to streptokinase in its pattern of activity and the generalized, rather than local manner in which they exert their plasminogen activation, is a major drawback in therapeutic use.

Single-chain urokinase (scuPA) and tissue plasminogen activator (tPA) are fibrin-specific thrombolytic agents and are thus expected to cause less bleeding complications resulting from a systemic fibrinogenolysis at doses that are therapeutically effective. While these plasminogen activators are more fibrin-specific, tPA has a short half-life in the patient, on the order of two to five minutes (Matsuo, (1982) *Throm Haemostas* 48:242) and the half-life of scuPA is similarly limited (Stump et al (1987) *J Pharm Exp Therap* 242(1):245–250).

Modification of these therapeutically useful plasminogen activators to increase the half-life while maintaining desired biological activities of the activators would allow the use of these activators in the mammalian fibrinolytic system in lower dosages to achieve comparable thrombolytic efficacy with the concomitant potential advantages of reduced proteolysis of plasma proteins, prevention of reocclusion for longer periods, and reduced production cost per therapeutic dose.

The problems of short half-life mentioned above and other undesirable properties of certain activators are well recognized and various modifications of the activators have been undertaken to solve them. These include the modification of tissue plasminogen activator (tPA) to prevent site specific N-glycosylation (Lau et al, (1987) *Biotechnology* 5:953–957) and identifying the function of the structural domains of tPA in order to construct second generation plasminogen activators with improved fibrinolytic activity (see for example, Klausner, (1986) *Biotechnology* 4:709–711 and references cited therein).

Clinical studies have shown that concurrent or subsequent administration of heparin with tPA therapy is recommended to keep blood clotting suppressed. Heparin is a conventional anticoagulant which is employed in conditions in which a rapid reduction in the coagulability of the blood is desired. The major disadvantage associated with heparin therapy is the principal toxic effect of hemorrhage.

The heparin molecule consists of (1-4)-linked 2-amino-2-deoxy-alpha-D-glucopyranosyl, alpha-L-idopyransyluronic acid and a relatively small amount of beta-D-glucopyranosyluronic acid residues.

Stassen et al, (1987) *Thromb Haemostasis* 58(3):947–950, describe the potentiation of thrombolysis by recombinant tPA and scuPA in the presence of high doses of two low molecular weight fractions of heparin.

Heparin has been bound covalently to solid supports to prepare blood-compatible surfaces. For example, PCT application WO86/03318 published Dec. 27, 1985 (Cardiol. Sci Center) discloses immobilization of urokinase on a heparin support to produce water-soluble complex with increased thrombolytic activity. The conjugation is via a carboxyl group, not an aldehyde group.

Paques et al, 1986 *Thromb Res* 42:797–807, describe an affinity complex formed between tPA or urokinase (uPA) and heparin. Apparently the heparin-binding site is related with the fibrin-binding site of these plasminogen activators.

It is desirable to conjugate the plasminogen activator to a smaller heparin fragment. Hoffman et al, (1983) *Carbohydrate Res* 117:328–331 discloses a method for producing heparin fragments using nitrous acid, wherein the fragments have 2,5-anhydro-D-mannose residues as reducing terminal units with aldehyde groups. Such aldehyde groups may be reacted with primary amines to give labile Schiff-bases which can be converted to stable secondary amines by reductive amination. Hoffman et al describes coupling of such heparin fragments to Sepharose and curdlan, a (1→3)-linked unbranched beta-D-glucan, and suggests coupling of heparin to human serum albumins and antithrombin.

U.S. Pat. No. 4,745,180 describes pharmaceutical compositions composed of water-insoluble proteins such as recombinant forms of beta-interferon, interleukin-2 or certain immunotoxins that are conjugated to at least one heparin fragment to produce a product which is water-soluble.

None of the references, however, disclose how to use heparin fragments to increase the half-life of plasminogen activators nor teach the targeting of heparin to the critical site of clot dissolution. Furthermore, it is not priori possible to predict which selected plasminogen activators would be favorable responsive, e.g., have good biological activity, to treatment with heparin fragments due to physical and pharmacokinetic differences among the plasminogen activators on the one hand, and albumins, cytotoxins and lymphokines, on the other hand.

SUMMARY OF THE INVENTION

Accordingly, the present invention provides for modifying plasminogen activators which have a systemic short half-life to prolong the presence of such proteins in the fibrinolytic system. As secondary advantages, the modification is expected to target heparin to the site of clot dissolution thereby introducing the anticoagulant properties of heparin to reduce reocclusion.

More specifically, the present invention is directed to a pharmaceutical composition comprising a non-toxic, inert, pharmaceutically acceptable carrier medium in which is dissolved a biologically active, selectively conjugated fibrin-specific plasminogen activator, wherein the fibrin-specific plasminogen activator is covalently conjugated via at least one of its lysine residues or amino-terminal amines to at least one heparin fragment having a terminal 2,5-anhydro-D-mannose residue through the aldehyde group of such residue, wherein the half-life of the plasminogen activator is prolonged.

Another aspect of the invention is a pharmaceutical composition comprising a non-toxic, inert, pharmaceutically acceptable carrier medium in which is dissolved a biologically active, selectively conjugated fibrin-specific plasminogen activator, wherein the fibrin-specific plasminogen activator is covalently conjugated via at least one of its lysine residues to at least one heparin fragment having a terminal 2,5-anhydro-D-mannose residue through the aldehyde group of such residue, wherein the conjugate targets the heparin component to the site of thrombis or emboli.

Yet a further aspect of the invention is a therapeutic method for treating a subject suffering from pulmonary embolism associated with myocardial infarction comprising, administering to said subject an amount of the pharmaceutical compositions described above which is effective to lyse fibrin and limit reocclusion.

Preferred embodiments of the plasminogen activators are recombinant tPA and scuPA.

BRIEF DESCRIPTION OF THE DRAWINGS

FIG. 1 is the amino acid sequence and corresponding DNA sequence of the gene designated cPA-P2 which encodes a hybrid plasminogen activator comprising plasminogen kringle 1, an urokinase linker and the urokinase protease domain, wherein the glycine residue at position 158 of urokinase has been replaced by lysine.

DESCRIPTION OF THE PREFERRED EMBODIMENTS

The tPA and urokinase herein may be obtained from tissue cultures or by recombinant DNA techniques, and from any mammalian source such as, e.g., mouse, primate, rabbit and human. Preferable such proteins are derived from a human source, and more preferable are recombinant, human proteins.

As used herein, the term "tissue plasminogen activator" designated as tPA, preferable human tPA, refers to a multi-domain serine protease. The cloning, expression, and analysis of recombinant tPA enabled its amino acid sequence to be elucidated and provides an abundant source of the protein (Pennica et al, (1983) *Nature* 301:214–221; Collen et al, (1984) *J Pharm Exptl Therap* 231:146–152).

As used herein, scuPA means a protein having a single amino acid chain and the characteristics of activating blood clot-associated plasminogen. Two forms of scuPA are known, one having a molecular weight of ~55,000 daltons (55 Kd) and the other weight of ~30,000 daltons (30 Kd). See Rijken et al, (1986) *Thrombosis Res* 47:761–763. Proteins having fibrinolytic activity have amino acid sequences as disclosed by Holmes et al (1985) *Biotechnology* 3:923–929, Jacobs et al (1985) *DNA* 4(2):139–146, Verde et al, (1984) *Proc Natl Acad Sci USA* 80:4727–4731, and Nagai et al (1985) *Gene* 36:185–188. As is clear from these sources, scuPA may vary in primary amino acid sequence without loss of the fibrin-selective characteristics of the protein.

One embodiment of the invention using scuPA employs a modified scuPA wherein the modified protein is incapable of forming two-chain urokinase (tcuPA). To make scuPA that is incapable of forming tcuPA, the amino acid sequence of scuPA is altered in the region of $lys_{158}$. Generally, $lys_{158}$ is converted to a neutral amino acid, such as glycine, that is resistant to proteolysis. See, e.g., EP 87311532.3, assigned to Cetus Corporation, and EP 200,451, published Nov. 5, 1986.

"Fibrin-specific" refers to those plasminogen activators which have a specific affinity for fibrin and will discriminate between circulating and fibrin-bound plasminogen.

The plasminogen activators described above also include modified forms of a recombinant protein provided the modified form retains fibrin specificity. Such modified plasminogen activator forms include those described in U.S. Ser. No. 132,206, filed Dec. 10, 1987, assigned to Cetus Corporation, which application is incorporated herein by reference. Among the novel plasminogen activators described therein are fibrinolytic proteins comprised of at least one domain capable of interacting with fibrin and the protease domain of urokinase. The domain capable of interacting with fibrin may have an amino acid sequence substantially the same as those of kringle 2 of tPA, kringle 1 and/or kringle 4 of plasminogen, and the finger domain of tPA. The protease domain may have an amino acid sequence substantially the same as that of 30 Kd urokinase.

The precise chemical structure of the proteins herein will depend on a number of factors. As ionizable amino and carboxyl groups are present on the molecule, a particular protein may be obtained as an acidic or basic salt, or in neutral form. All such preparations which retain their bioactivity when placed in suitable environmental conditions are included in the definition of proteins herein. Further, the protein molecule may be augmented by derivatization using sugar moieties (glycosylation) or by other supplementary molecules such as lipids, phosphate, acetyl groups and the like, more commonly by conjugation with saccharides. Certain aspects of such augmentation are accomplished through post-translational processing systems of the producing host; other such modifications may be introduced in vitro. In any event, such modifications are included in the definition of these proteins herein so long as the bioactivity of the protein is not destroyed. It is expected, of course, that such modifications may quantitatively or qualitatively affect the bioactivity by either enhancing or diminishing the activity of the protein in the various assays.

The term "selectively conjugated" as used herein to apply to the plasminogen activator enzymes refers to proteins which are covalently bonded via one or more of the lysine residues of the enzyme or amino-terminal amines. The number of lysine residues to which the heparin fragment is bound depends mainly on the reaction conditions, the ultimate use, and the particular protein employed. The lysine is generally linked to the heparin fragment(s) through the free epsilon-amino group of the lysine.

According to the process of this invention, the half-lives of the plasminogen activators described above, which are normally short, are prolonged by modifying the enzymes through conjugation to the reactive aldehyde group of a heparin fragment. The pH of the reaction is preferably about 6 to 8, more preferably 7-7.5. The success of such a modification of these plasminogen activators cannot be predicted from earlier use of the heparin modification of other enzymes or proteins.

The heparin fragment to which the protein is attached has a wide range of molecular weights generally between about 10,000 and 20,000, with an average of about 16,000. In addition, the heparin fragment contains a 2,5-anhydro-D-mannose residue as the reducing terminal unit. The unit has an aldehyde group which is not involved in intramolecular hemiacetal formation.

The chemistry of the reaction between the lysine(s) of the protein formation and the aldehydes(s) of the heparin fragment involves formation of labile Schiff bases which convert into stable secondary amines under reducing conditions. Therefore, if the aldehyde qroups are present as cyclic hemiacetals, the Schiff base does not form as readily, thereby reducing yields. As a result, the heparin fragment herein must have terminal units with aldehydes which do not form cyclic hemiacetals.

The heparin fragments are produced by partially depolymerizing heparin by deaminative cleavage to produce terminal aldehyde groups as defined above. Any oxidizing reagent which effects such deamination may be employed, such as, e.g., nitrous acid, which is preferred. Nitrous acid may be prepared by adding sodium nitrite solution to the heparin in acid (e.g., HCl, acetic acid). The depolymerization preferably takes place at room temperature for one to three hours.

Once the fragmentation has occurred, the fragments of low molecular weight are separated from the reaction mixture, as by using dialysis. The dialyzed fragments are then reacted with the protein, preferably at 37° C., and preferably for 10–30 hours, depending, for example, on the protein, in an aqueous solution, preferably at a pH of about 6–8. A reducing agent may be present in the reaction vessel or may be added after the heparin is conjugated to the protein. If the reducing agent is present at the same time, it must not adversely affect the reaction and is preferably sodium cyanoborohydride. If the reducing agent is added afterward, it may be any reducing agent which will reduce the Schiff base without damaging the protein, e.g., sodium borohydride.

After the reaction, the reaction mixture is treated to separate its components, as by transferring to a size exclusion column. The column is washed appropriately using a buffer. The fractions from the column corresponding to the conjugates re identified by molecular weight and the protein may be identified by ultraviolet analysis. The protein is tested for water-solubility and biological activity. Preferably, at least about 10%, more preferably 25%, more preferably 50%, and most preferably 100% of the biological activity of the protein is retained.

The protein thus modified is then formulated in a non-toxic, inert, pharmaceutically acceptable aqueous carrier medium, preferably at a pH of about 3 to 8, more preferably 6–8. Aqueous formulations compatible with the culture or perfusion medium will generally be used. For use in in vivo therapeutic applications, the sterile product will consist of a mixture of protein dissolved in an aqueous buffer in an amount which will provide a pharmaceutically acceptable pH when the mixture is reconstituted. A water-soluble carrier such as mannitol may optionally be added to the medium.

The dosage level of the protein in the formulation will depend on the in vivo efficacy data obtained after preclinical testing and will depend mainly on the protein employed and ultimate use. Generally, the efficacious dosage of recombinant tPA currently administered in humans in acute myocardial infarction can exceed 100 mg (Verstraete et al, (1985) *Lancet* 1:842–847); this is due in part to its short systemic half-life. The present composition, having a longer half-life, is administered for this same therapy in 10- to 20-fold reduced dosages. The reduced dosage also decreases the tendency for bleeding at distant sites, a side effect observed in clinical studies using 100–150 mg dosages of recombinant tPA.

If the formulation is lyophilized, the lyophilized mixture may be reconstituted by injecting into the vial a conventional parental aqueous injection such as, i.e., distilled water.

The reconstituted formulation prepared as described above is suitable for parenteral administration to humans or other mammals in therapeutically effective amounts (i.e., amounts which eliminate or reduce the patient's pathological condition) to provide thrombolytic therapy thereto. A preferred route of administration is by intravenous infusion, wherein a bolus infusion of ~60% of the total dosage is administered in the first hour, followed by equal aliquots of the remaining dosage over the next two hours.

The compositions of the present invention are effective in the treatment of thromboembolic disease. These indications include lysis of pulmonary emboli, deep vein thrombi, arterial thrombi and emboli, and acute coronary artery thrombosis (by intracoronary injection) associated with acute myocardial infarction.

In the following examples, which illustrate the invention further, all parts and percentages are by weight unless otherwise noted, and all temperatures are in degrees Celsius.

EXAMPLE I

Preparation of Heparinized PA

A. Preparation of Heparin Fragments

To a total of 0.76 g of commercially obtained heparin in 40 ml water was added 0.1M HCl until the pH was 2.5. A solution of 6 mg of sodium nitrite in 1.0 ml water was added dropwise to the heparin solution, and the reaction mixture was stirred at room temperature for two hours. After this time the pH of the reaction mixture was adjusted to 6.5–7 with 0.1M sodium hydroxide, and the solution was concentrated under reduced pressure to about 10 ml. The concentrate was dialyzed against distilled water and freeze-dried to yield 0.36 g of fragmented heparin preparation.

B. Conjugation of Heparin Fragments to PA

Recombinant PA obtained by expression of a hybrid plasminogen activator gene in bacterial cells was employed in this example. The hybrid PA gene is described in U.S. Ser. No. 132,206, supra, and incorporated herein by reference. The gene, cPA-P2, comprises DNA encoding plasminogen kringle 1, a urokinase linker and the urokinase protease domain (with lysine substituted at urokinase residue 158). Generally, plasmid pLP19, a baculovirus transfer vector, containing the cPA-P2 gene, was constructed as follows.

The plasmid pPD18 (ATCC 67431), a baculovirus transfer vector, was digested with NcoI and NotI; the resulting fragments were separated by electrophoresis through low melting point agarose and the large fragment encoding most of a urokinase-like protease domain was isolated. This fragment was ligated to the oligonucleotides JD90, JD91, JD92, and JD93 described in Table 1 below. These four oligonucleotides anneal together to form a double-stranded segment of DNA with a single-strand extension at both ends; one of these ends is compatible with the single strand created by the enzyme NcoI and the other end is compatible with the single strand generated by the enzyme NotI. After ligation, the mixture was heated to 65° C. for 5 minutes, diluted from 20 ul to 200 ul with 10 mM Tris pH 7.5, 1 mM EDTA, cooled to room temperature, and used to transform competent *E. coli* (strain MM294) cells. A colony containing pPD20 was identified by restriction mapping.

pPD20 was digested with XmaI and NotI. The large fragment was isolated from low melting point agarose after electrophoresis. This segment was ligated to oligonucleotides JD94, JD95, JD96 and JD97 described in Table 1 below. These four oligonucleotides anneal to form a double-stranded segment of DNA with single-stranded XmaI and NotI extensions. After ligation, *E. coli* strain MM294 were transformed and a colony containing pPD21 was isolated by hybridization with JD96. The oligonucleotide-derived DNA in pPD21 was sequenced and found to contain two incorrect bases, even though the oligonucleotides used above contained the correct sequence. The errors were in the region encoding the signal sequence (corrected with oligonucleotide JD123) and in kringle 1 of plasminogen (corrected with oligonucleotide JD124).

These errors were corrected by in vitro mutagenesis. This was done by placing the small EcoRV-EcoRI fragment of pPD21 in the vector M13mp19 that had been digested with HincII and EcoRI, thereby creating mpJD18. Single-stranded mpJD18 was prepared and used as a template for the mutagenic oligonucleotide JD123. A phage with the correct sequence was isolated by hybridization with JD123 and termed mpJD18-123; single-stranded DNA was prepared from this phage and used as a template for the mutagenic oligonucleotide JD124. A phage containing the corrections made by both JD123 and JD124 was then identified by hybridization with JD124 and designated mpJD18-123/124. The NotI-NcoI fragment of mpJD18-123/124 that encodes the plasminogen kringle 1 was isolated from low melting point agarose after electrophoresis. This fragment was ligated to the large NcoI-NotI fragment of pPD18 that had been isolated from low melting point agarose after electrophoresis. Competent *E. coli* (strain MM294) cells were transformed with this ligation mixture and pJD22 was identified by restriction mapping.

Plasmid pLP19 was subsequently constructed using the oligonucleotide JD89B, illustrated in Table 1, for site-specific mutagenesis to change gly→lys at the position corresponding to $lys_{158}$ urokinase of the gene encoding the hybrid PA in plasmid pJD22.

TABLE 1

| Oligonucleotide Number | Sequence |
|---|---|
| JD89B | GCCGCGCTTTAAGATTATTGGGGG |
| JD90 | CATGGCGTTAGCTATTACTCTTGCATTATTGCTTCTCCTACTGTTAT<br>TGCCTGGGTGTTGGGCTAGCGAATGCAAAACCGGTGACGGTA |
| JD91 | AAAACTACCGTGGTACCATGTCCAAAACCAAAAACGGTATCACCTGC<br>CAGAAATGGTCCTCCACCTCCCCGCACCGTCCGCGTTTCTCCCCGGG<br>ATGGCGC |
| JD92 | GGCCGCGCCATCCCGGGGAGAAACGCGGACGGTGCGGGGAGGTGGAG<br>GACCATTTCTGGCAGGTGATACCGTTTTTGGTTTTGGACATGGTACC |
| JD93 | ACGGTAGTTTTTACCGTCACCGGTTTTGCATTCGCTAGCCCAACACC<br>CAGGCAATAACAGTAGGAGAAGCAATAATGCAAGAGTAATAGCTAAC<br>GC |
| JD94 | CCGGCTACCCACCCGTCCGAAGGTCTGGAAGAAAACTACTGCCGTAA<br>CCCGGACAACGACCCGCAGGGTCCGTGGTGCTACACCACCGACCCGG<br>AA |
| JD95 | AAACGTTACGACTACTGCGACATCCTCGAGTGCGAAGAAGAACCGTC<br>CTCCCCGCCGGAAGAACTGAAATTCCAGTGCGGTCAGAAAACCCTGC |
| JD96 | GGCCGCAGGGTTTTCTGACCGCACTGGAATTTCAGTTCTTCCGGCGG<br>GGAGGACGGTTCTTCTTCGCACTCGAGGATGTCGCAGTAG |
| JD97 | TCGTAACGTTTTTCCGGGTCGGTGGTGTAGCACCACGGACCCTGCGG<br>GTCGTTGTCCGGGTTACGGCAGTAGTTTTCTTCCAGACCTTCGGACG<br>GGTGGGTAG |

*S. frugiperda* insect cell cultures were infected with plasmid pLP19 containing the coding sequences for the hybrid PA. The culture was harvested 48–72 hours after infection. The cells were removed by filtration and the culture medium concentrated 10-fold by ultrafiltration.

The concentrated culture medium was stepwise filtered through a series of membranes with decreasing pore size to remove cell debris. The filtrate was applied to hydroxyapatite (HA) resin either in a chromatographic column or through batch adsorption. PA was eluted by a linear gradient of increasing concentrations of phosphate (column) from 0.01M to 1.0M phosphate or step washes of buffers with increasing phosphate concentration. Plasminogen activation activity was determined on casein/agarose plates containing plasminogen as described in Saksela (1981) *Analytical Biochem* 111:276–282. Briefly, petri dishes are prepared with an agarose medium containing 100 ml of medium, which contains 37.5 ml dH$_2$O, 10 ml 10×phosphate buffered saline, 40 ml 2.5% agarose, 12.5 ml of 8% boiled powdered milk and 1000 ug of plasminogen (Calbiochem #528175) in 20 mM Tris-HCl, pH 8. The boiled powdered milk is prepared by boiling an 8 g/100 ml dH$_2$O solution of milk for 20 minutes; centrifuging 20 min at 10,000×g and retaining the supernatant. The liquid agarose solution is added at 65° C.; plasminogen is added when the mixture has cooled, but not hardened. 20 ml is added to a 100 mm petri dish. To assay plasminogen activation, 20 ul of solution containing a plasminogen activator is placed in 4 mm holes punched in the casein agarose, and incubated at 37° C. for 2–24 hours. The radius of the lysis halo that forms as the casein is degraded by plasmin is in proportion to the log of the amount of plasminogen activator that was placed in the well. A standard plasminogen activator, such as urokinase, is used to calibrate the assay. Fractions containing the peak PA activity were pooled.

The pooled fractions from HA were applied onto a Cibacron blue affinity column. Bound protein was eluted with a linear gradient of arginine from 0.0M arginine to 1.0M arginine. Fractions containing peak PA activities are pooled and desalted over a gel permeation column. Sephacryl S200 is a desired resin for this step since it can also serve to remove large aggregates of PA from the monomeric PA and achieve buffer exchange all in the same step. Peak fractions containing highly purified PA molecules as examined by SDS/PAGE and immunoblot of the SDS/PAGE are obtained and used for conjugation with heparin fragments.

To a solution of 2.0 mg of the recombinant PA produced above in 1 ml 0.1M sodium phosphate buffer, pH 7.5 is added 5 mg of the heparin preparation and 2 mg NaCNBH$_3$. The solution is mixed thoroughly and kept overnight (16–18 hours) at 37° C.

Alternative embodiments of the plasminogen activator which could be substituted in this example include recombinant tPA obtained by expression of human tPA cDNA in eucaryotic cells (as described by Pennica et al, supra), any of the hybrid PAs disclosed in U.S. Ser. No. 132,206, supra, or scuPA obtained from the conditioned media of a transformed kidney cell line (Sandoz AG, Switzerland).

C. Isolation of Heparin Modified PA

The reaction mixture is applied to a Biogel P6DG column and eluted with 0.1M sodium phosphate buffer, pH 7.0 to remove NaCNBH$_3$ and unreacted PA. Analysis using a DuPont GF-250 sizing column shows a molecular weight in the range of about 180,000–200,000 daltons. The purification of the heparin-PA conjugate depends upon the apparent molecular weight of the conjugate. The apparent molecular weight as estimated from a sizing column, calibrated for globular molecules such as proteins, is much larger than the actual molecular weight due to the heparin moiety(s). Aliquots of the fractions are assayed for plasminogen activation activity using casein/agarose plates containing plasminogen as described above.

EXAMPLE II

Characterization of Heparinized PA

A. Bioactivity of Heparinized PA

The thrombolytic properties of PA in rabbits with experimental jugular vein thrombosis (described by Gurewich et al (1984) *J Clin Invest* 73:1731–1739) provides one means for in vivo characterization of the heparinized PA. $^{125}$I-labeled clots are prepared from delipidated rabbit plasma in the jugular veins of anesthetized New Zealand white rabbits. Blood samples are withdrawn at intervals during and after the infusion of the plasminogen activator. The plasma samples are analyzed for solubilized $^{125}$I-counts indicative of the release of fibrin fragments. The control is a measure of released radioactive material in plasma of rabbits injected with the control buffer (0.3M NaCl and 0,01% Tween). PA activity in the samples is determined by using the indirect amidolytic assay which uses the chromogenic substrate S2251 (Kabi) to measure amidolytic activity (Verheijen et al, (1982) *Thromb Haemostas* 48:266–269). An increase in the level of amidolytic activity, over the entire time course, is observed in rabbits infused with heparinized tPA when compared to native tPA.

B. Determination of Half-Life

The half-life of the PA-heparin conjugate is determined in rabbits according to the procedure of Lau et al (1987) supra. Anesthetized New Zealand white rabbits (2–2.5 kg) are infused through the marginal ear veins with a bolus of 45–250 ug/kg of heparin-modified PA or native tPA followed by continuous infusion of tPA for 15 or 110 minutes. One ml blood samples are withdrawn from the carotid artery directly into 3.8% sodium citrate at time zero and for set time intervals (1, 2, 3, 4, 5, 7, 10, 15, 20, 30, 45, and 60 min). The samples are centrifuged to obtain cell-free plasma and frozen until analyzed by ELISA, indirect amidolytic, and $^{125}$I-fibrinolytic assays. Each PA is tested in at least three rabbits. Kinetic analysis of the data is then performed. The results provide confirmation that the heparinized PA exhibits a longer systemic half-life while retaining its biological activities.

In summary, the present invention provides a pharmaceutical composition wherein a biologically active fibrin-specific plasminogen activator is selectively conjugated to a heparin fragment to prolong the systemic half-life of the activator. In addition, the conjugate delivers heparin directly to the site of the pulmonary embolism and thereby reduces the incidence of systemic bleeding commonly associated with heparin therapy.

Various modifications of the above-described modes for carrying out the invention which are obvious to those skilled in the field of protein conjugation, pharmaceutical formulation or related fields are intended to be within the scope of the following claims.

What is claimed is:

1. A pharmaceutical composition comprising a nontoxic, inert, pharmaceutically acceptable carrier medium in which is dissolved a biologically active selectively conjugated fibrin-specific tissue plasminogen activator, wherein the fibrin-specific tissue plasminogen activator is covalently conjugated via at least one of its lysine residues or amino-terminal amines to at least one heparin fragment having a terminal 2,5-anhydro-D-mannose residue through the aldehyde group of such residue, wherein the half-life of the tissue plasminogen activator is prolonged and the conjugate targets the heparin component to the site of thrombis or emboli.

2. The composition of claim 1 wherein the fibrin-specific tissue plasminogen activator is derived from a mammalian source.

3. The composition of claim 1 wherein the tissue plasminogen activator is a recombinant protein from a human source.

4. The composition of claim 3 wherein the recombinant tissue plasminogen activator comprises at least one domain capable of interacting with fibrin and a protease domain substantially homologous with the protease domain of urokinase.

5. The composition of claim 4 wherein the domain capable of interacting with fibrin comprises an amino acid sequence selected from the group consisting of lysine-binding kringle domains and finger domains.

6. The composition of claim 5 wherein said lysine-binding kringle domain is substantially homologous with one selected from the group consisting of kringle 2 of tPA, kringle 1 of plasminogen and kringle 4 of plasminogen.

7. A therapeutic method for treating a subject suffering from thromboembolic disease comprising, administering to said subject an amount the pharmaceutical composition of claim 1 effective to lyse fibrin and limit reocclusion.

8. The method of claim 7 wherein the thromboembolic disease is associated with myocardial infarction.

9. The method of claim 7 wherein the plasminogen activator is a recombinant protein from a human source.

* * * * *